(12) United States Patent
Wilson et al.

(10) Patent No.: US 6,395,555 B1
(45) Date of Patent: May 28, 2002

(54) METHOD AND APPARATUS FOR DETERMINING THE EFFECT OF A DRUG ON CELLS

(76) Inventors: David F. Wilson, 207 St. Marks Sq.; Sergei A. Vinogradov, 4405 Osage Ave., both of Philadelphia, PA (US) 19104

(*) Notice: Subject to any disclaimer, the term of this patent is extended or adjusted under 35 U.S.C. 154(b) by 0 days.

(21) Appl. No.: 09/418,104

(22) Filed: Oct. 14, 1999

(51) Int. Cl.[7] ................... G01N 33/50; G01N 31/00

(52) U.S. Cl. .............................. 436/68; 436/2

(58) Field of Search .................. 250/484.1, 486.1, 250/487.1

(56) References Cited

U.S. PATENT DOCUMENTS

| | | |
|---|---|---|
| 4,476,870 A | 10/1984 | Peterson et al. |
| 4,947,850 A | 8/1990 | Vanderkooi et al. |
| 5,186,173 A | 2/1993 | Zuckerman |
| 5,279,297 A | 1/1994 | Wilson et al. |
| 5,284,831 A | 2/1994 | Kahl et al. |
| 5,495,850 A * | 3/1996 | Zuckerman ................. 128/634 |
| 5,501,225 A | 3/1996 | Wilson |
| 5,515,864 A | 5/1996 | Zuckerman |
| 5,830,138 A | 11/1998 | Wilson |
| 5,908,776 A | 6/1999 | Burbaum et al. |

OTHER PUBLICATIONS

Motterlini et al. Depression of Endothelial and Smooth Muscle Cell Oxygen Consumption by Endotoxin; American Journ. of Physio. vol. 275, No. 168 p. 776–782, Sep. 1998.*

Ince et al. Microcirculatory Oxygenation and Shuntingin Sepsis and Shock; Crit. Care Med. vol.27, No.7 pp. 1369–1377, Jul. 1999.*

Eagle, "Nutrition Needs of Mammalian Cells in Tissue Culture", *Science* 122:501–504 (1955).

Eagle, "Amino Acid Metabolism in Mammalian Cell Cultures", *Science* 130:432–437 (1959).

Lo et al., "Calibration of Oxygen–Dependent Quenching of the Phosphorescence of Pd–meso–tetra (4–Carboxyphenyl) Porhine: A Phosphor with General Application for Measuring Oxygen Concentration in Biological Systems", *Analy. Biochem.* 236:153–160 (1996).

Pawlowski et al., "Monitoring of the Oxygen Pressure in the Blood of Live Animals Using the Oxygen Dependent Quenching of Phosphorescence", *Adv. Exp. Med. Biol.* 316:179–185 (1992).

Robiolio et al., "Oxygen diffusion and mitochondrial respiration in neuroblastoma cells", *Am. J. Physiol.* 256 (6 Pt 1):C1207–1213 (Jun. 1989).

Shrager, "Quadratic Programming for Nonlinear Regression", *Numerical Mathematics* 15:41 (1972).

(List continued on next page.)

Primary Examiner—Jon P. Weber
Assistant Examiner—Patricia Patten
(74) Attorney, Agent, or Firm—Evelyn H. McConathy; Dilworth Paxson LLP (57) ABSTRACT

A method is described for determining the effect of a drug or drugs on an attached culture of cells comprising (i) dissolving the phosphorescent compound, of known or predetermined quenching constant and lifetime at zero oxygen, in a culture medium at a selected temperature comprising an attached culture of test cells; (ii) introducing the drug(s), whose effect on the test cells is to be determined, into the culture medium; (iii) illuminating the culture medium with pulsed or modulated light at a level sufficient to cause the phosphorescent compound to emit measurable phosphorescence; (iv) measuring the emitted phosphorescence; and (v) calculating the phosphorescence lifetime and oxygen concentration gradient in the medium, thereby determining the effect of the drug on the respiration rate of the cells at the selected temperature. Apparatus for carrying out the method is also disclosed.

27 Claims, 4 Drawing Sheets

OTHER PUBLICATIONS

Vanderkooi et al., "An Optical Method for Measurement of Dioxygen Concentration Based upon quenching of Phosphorescence", *J. Biol. Chem.,* 262 (12):5476–5482 (Apr. 1987).

Vanderkooi et al., "A New Method for Measuring Oxygen Concentration of Biological Systems", in Oxygen Transport to Tissue VIII, Longmuir, ed., Plenum (Aug. 1986).

Wilson et al., "Effect of Hyperventilation on Oxygenation of the Brain Cortex of Neonates", *Adv. Exp. Med. Biol.* 316:341–346 (1992).

Wilson et al., "The Oxygen Dependence of Mitochondrial Oxidative Phosphorylation Measured by a New Optical Method for Measuring Oxygen Concentration", *J. Biol. Chem.,* 263:2712–2718 (1988).

* cited by examiner

METHOD AND APPARATUS FOR DETERMINING THE EFFECT OF A DRUG ON CELLS

GOVERNMENT SUPPORT

This work was supported in part by grants from the National Institutes of Health, including grant numbers NS-31465, HL-60100 and CA-74052. The government may have certain rights in this invention.

FIELD OF THE INVENTION

This invention relates to methods and apparatus for determining the effect of a drug on viable animal or plant cells in culture.

BACKGROUND OF THE INVENTION

The in vitro screening of the effects of drugs on human or other live animal cells requires techniques in which large numbers of samples can be measured with minimal consumption of labor and time. Current technology involves growing the cells in culture in multi-well plates that permit the medium to be changed as required and the cells measured using automated plate readers. The evaluation of drug effects generally involves treatment of the cells with a selected drug or combination of drugs as a single administration or over a predetermined time course. This is followed by a determination of the viability of the cells in response to the drug, and an assessment of the efficacy and safety of the drug.

Unfortunately, many of the assessment techniques currently available are subjective determinations, although they are typically based upon objective measurements. For example, cells are typically stained with a selected dye or dyes or by some other staining technique to determine whether the cells are alive or dead following exposure to the test drug. However, in some cases the dyes and staining techniques introduce their own set of variables into the assessment. Although useful, a dye may also introduce certain disadvantages to the evaluation of a drug, e.g., the dye, even if biocompatible, could affect the speed, accuracy, toxicity, and visible coloration of the medium. Regardless of whether the affect is a disadvantage or an enhancement to the effect of the drug being tested, the simple fact that unknown variable could affect the outcome makes the final determination of the drug analysis subjective and of questionable reliability.

Cellular oxygen consumption is a reliable measure of cell physiology. Viable cells require continuous consumption of oxygen in order to survive, metabolize, grow and divide. Under constant temperature and culture conditions, the rate of oxygen consumption for a particular cell type is proportional to the number of cells. Thus, the rate of oxygen consumption provides an accurate measure of the number of live cells. Changes in cell number by either cell death or growth inhibition can be measured. Although others have attempted to measure oxygen concentrations to provide information regarding tissues and other in vivo environments, e.g., Vanderkooi et al, *J. Biol. Chem.*, 262 (12):5476–5482 (April 1987); U.S. Pat. Nos. 4,476,870; 4,947,850; 5,186,173; 5,515,864, there has remained a need in the art for methods and apparatus that will more quickly, more accurately, and more economically determine the effect of drugs on a variety of tissues and cell types in a reliable and reproducible manner.

SUMMARY OF THE INVENTION

The present inventors have responded to the need for an improved, reliable and fast way of testing the effect of a drug or drugs on a variety of tissues and cells types by developing methods and apparatus that utilize the rate of respiration of a selected population of cells to provide a measure of the metabolic disturbance (uncoupling, inhibition, stimulation) of the cells in response to exposure to the selected drug or drugs.

In accordance with one aspect of the present invention, there is provided a method for determining the effect of a drug on attached cultures of cells comprising the following steps. A phosphorescent compound is dissolved in a culture medium containing an attached culture of cells, wherein quenching constant and lifetime at zero oxygen of the compound are known or previously determined at a selected, constant temperature. A drug, whose effect on the cells is to be tested or determined, is introduced into the culture medium either before the medium is added to the cells or while the medium is in situ over the cells. Then, the cell culture, comprising the cells, cell culture medium, phosphorescent compound and test drug, is illuminated with a pulsed or modulated excitation light at an intensity and frequency sufficient to cause the phosphorescent compound to emit a measurable phosphorescence. The emitted phosphorescence is then measured; and the phosphorescence lifetime and oxygen concentration gradient in the medium are calculated, thereby permitting a fast and reproducible objective determination of the effect of the drug on the respiration rate of the cells at the constant temperature.

In a preferred embodiment of the invention, the phosphorescent compound is selected or prepared which does not chemically react with the cells or the culture medium, nor does it affect the growth, viability or morbidity of the cells.

In additional embodiments of the invention, one or more of the preceding steps may be repeated as necessary to provide the measurements needed to calculate a phosphorescence distribution profile for the drug being tested. In preferred embodiments, the illumination, measurement and calculation steps are repeated for same cell culture, or multiple matched cell cultures are established to permit comparisons of a variety of drugs, drug combinations, or drug concentrations.

In a preferred embodiment of the invention, the attached cells are animal cells. The cells can be primary or secondary cultures, differentiated or undifferentiated, transformed, transfected, engineered or recombinant cells, or the like, as applicable to the drug or substance being tested. The cells can be attached as confluent monolayers, as actively dividing cells, or at any point in their life cycle. The method is designed to negate the metabolic status of the cells before the drug is added, by the use of mathematical constants based on matched control cell cultures in the calculation of the resulting respiratory rate of the cells in response to the added drug.

In another embodiment of the invention, the method comprises determining (i) the mean partial pressure of oxygen in the culture medium, and (ii) any change in partial pressure, thereby permitting the determination of any change in the respiration rate of the cells in response to the added drug. The oxygen distribution or concentration gradient is calculated for the entire depth of the culture medium, extending from the attached cell layer to the air/medium interface. Determination of the distribution curve of oxygen concentrations throughout the culture medium, permits the determination of respiration rate of the cells. Moreover, the change of mean partial pressure is used to determine morbidity of the cells, growth of the cells, or metabolic alteration of the cells, in response to the drug.

In yet another embodiment of the invention, the excitation light is provided by a light source selected from the group consisting of flash lamp, pulsed light emitting diode, and pulsed laser to illuminate the culture medium at a selected frequency.

In an additional embodiment of the invention, the emitted phosphorescence is measured by a time domain device or by a frequency domain device. In preferred embodiments the emitted phosphorescence is measured by means of a device, such as a photomultiplier, an avalanche photodiode, or a photodiode.

In yet another embodiment of the invention, the measured phosphorescence values are converted into digital values.

In a further embodiment, the rate of oxygen consumption of the cells is calculated by a process which comprises reconstructing the oxygen concentration gradient by deconvoluting the distribution of phosphorescence lifetime data into an underlying distribution of exponentials. Reconstruction of the oxygen concentration gradient permits determination of the rate of oxygen consumption of the cells following exposure to the test drug.

In certain embodiments of the invention, the phosphorescent compound is a porphyrin compound, preferably having the formula:

wherein $R_1$ is a hydrogen atom or a substituted or unsubstituted aryl; $R_2$ and $R_3$ are independently hydrogen or are linked together to form substituted or unsubstituted aryl; and M is a metal. In preferred embodiments of the invention, M represents a metal selected from among Zn, Al, Sn, Y, La, Lu, Pd, Pt or derivatives thereof In additional embodiments of the invention, the porphyrin is selected from among of tetrabenzoporphyrins, tetranaphthoporphyrins, tetraanthraporphyrins, or derivatives thereof In a preferred embodiment, the porphyrin is selected from among the following compounds: a meso-tetraphenylated derivative; a tetraphenyltetrabenzoporphyrin; a tetraphenyltetranaphthoporphyrin; a meso-tetra-(4-carboxylphenyl)porphyrin; a meso-tetraphenyltetrabenzoporphyrin; a meso-10 tetraphenyltetranaphthoporphyrin; and a tetrabenzoporphyrin.

In yet additional embodiments, the porphyrin is a first, second, third, fourth or fifth generation dendrimer, particularly wherein the dendrimer comprises polyglutamate dendritic cages.

In accordance with another aspect of the present invention, there is provided an apparatus for determining the effect of a drug on attached cultures of cells comprising the following elements: a) a means for illuminating the cell culture, comprising the cells, cell culture medium, a phosphorescent compound and a test drug at a selected, constant temperature, preferably with a pulsed or modulated light, at an intensity and frequency sufficient to cause the medium-contained phosphorescent compound to emit a measurable phosphorescence; b) a means for measuring the emitted phosphorescence; and c) a means for calculating the phosphorescence lifetime and oxygen concentration gradient in the medium, thereby quickly, reproducibly and objectively determining the effect of the drug on the respiration rate of the cells at the selected temperature. The preferred means for illumination comprises a time domain device or a frequency domain device.

In another embodiment of the invention, the apparatus means for measuring the emitted phosphorescence comprises a phosphorometer, and in yet another embodiment further comprises a digital signal processor.

In certain additional embodiments of the invention, the method or apparatus further comprises a high sensitivity video camera for measuring the emitted phosphorescence from the phosphorescent compound. One or more steps of the method or apparatus may also be automated.

The invention will be more fully understood from the following detailed description of referred embodiments, drawings and examples, all of which are intended to be for illustrative purposes only, and not intended in any way to limit the invention.

DETAILED DESCRIPTION OF THE INVENTION

The present invention comprises a method and apparatus for determining the effect of a drug on attached cultures of cells in a culture medium. The present invention uses the phenomenon of oxygen dependent quenching of phosphorescence, combined with non-toxic, soluble phosphors, and provides an efficient, reliable and economical method and apparatus to quickly and quantitatively determine the respiratory activity of cells and their metabolic state. The invention uses a phosphorescent compound having a known quenching constant and known lifespan at zero oxygen for a given temperature. Repeated measurements can be used as a quantitative analysis of the time course of alterations in cell number in response to changed conditions in the cell medium. If the quenching constant and lifespan are unknown for a particular cell type or phosphor, values can be determined by calibrating the quenching constant and lifetime at zero oxygen for the compound.

In practice, the method of the present invention comprises the following steps and elements. Non-toxic phosphorescent compounds are dissolved in the culture medium of a layer of attached cells. A drug, for which the effect on the test cells is being determined, is introducing into the culture medium of each sample. Then, the culture medium is illuminated with pulsed or modulated light to raise the phosphorescent molecules to an excited state, and the resulting phosphorescent light is measured in the quiescent (undisturbed) medium under constant conditions (fixed temperature, oxygen pressure, nutrients and the like). The decay constant is calculated from the resultant measurements; thereby permitting a determination of the oxygen concentration in the medium.

If the mean oxygen concentration is the same as that of air, then the cells have ceased respiration and are no longer viable. However, given that the cells are alive and metabolizing oxygen from the culture medium ("viable"), the mean oxygen concentration in the medium will reproducibly measure below that of the oxygen concentration in the air at the surface of the medium, which, of course, is the same as the surrounding air. Once the oxygen gradient has been determined, standard incubation conditions can be resumed and continued until the next measurement is desired, at which point the process can be repeated as necessary.

The invention relies upon the principle that oxygen infuses into the medium at the air/medium interface and diffuses throughout the medium. Accordingly, the oxygen, which is adjacent to the layer of cells attached to the bottom of the chamber, is consumed by cellular respiration. As a result, the oxygen concentration (or pressure) will be lower in the medium at the bottom of the chamber than in that at the top (air/culture medium interface). Thus, the difference in oxygen concentration per unit depth (thickness) within the cell culture medium is a function of the diffusion constant for oxygen in the medium and the rate of oxygen consumption by the cells.

In certain preferred embodiments of the invention, the rate of oxygen consumption by the cells can be determined from the measured phosphorescence by calculating the diffusion gradient throughout the cell culture medium between the attached cell layer and the air/medium interface at the surface of the medium. Such embodiments include deconvolution of the measured light data, and result in more sensitive test data. Moreover, the oxygen concentration can be determined one or more times after the treatment with the drug, or it can be determined both before and after drug therapy to facilitate a comparison.

Hence, the apparatus of the present invention comprises a means for illuminating the culture medium with pulsed or modulated light at an intensity sufficient to cause measurable emitted phosphorescent light from the phosphor(s) within the medium; a means for measuring and quantifying the emitted phosphorescent light; and a means for calculating the phosphorescence lifetime (decay) of the emitted light, thereby permitting the determination of the oxygen concentration (gradient) in the medium.

I. The Cell Culture, Media and Growth Conditions

In accordance with the present invention the effect of a drug or other medicament can be tested on any type of live animal or plant cells, although the invention is not presently intended to apply to microbial cells. Mammalian cells, especially human cells, are the type which are most often used for drug testing, and so are the type for which this invention is most applicable. However, the invention could also be extended to bird, rodent, fish, amphibian, insect or any other type of non-microbial cells in culture.

The cells most suitable for the present invention are those cells which can be cultured under constant and reproducible cell culture conditions, and which grow in culture as an attached monolayer. The cells can be dividing, quiescent or senescent or at any point of viability, ranging from inoculation through death. Similarly, the confluence of the cell monolayer cells is irrelevant to the present method. This is because the measurement of phosphorescence is compared against a constant. Thus, the present method is particularly suited for determining the status of the cells e.g., following exposure to a drug; that is, for determining whether they are actively dividing, completely dead or at some degree of viability in between.

The cell type being cultured may be selected for testing based upon whether the drug is intended for human or veterinary uses, or other uses. The cells can be primary or secondary cultures, differentiated or undifferentiated, transformed, transfected, engineered or recombinant cells, or the like, as applicable to the substance being tested.

The cells are typically attached to the bottom of a culture dish, plate or well. Accordingly, an attached layer of cells, covered with undisturbed growth medium, having a depth of at least about 1 mm, and open to the air (albeit at times through an oxygen permeable plastic cover) generates an oxygen diffusion gradient as the oxygen enters the medium at the air/medium interface and diffuses to the cells, where it is consumed. The higher the rate of oxygen consumption by the cells, the lower the oxygen pressure in the layer of medium adjacent to the cells, and the larger the gradient in oxygen from the cell layer to the air/medium interface.

The method can also be adapted to cells attached to glass beads or other suitable surfaces, so long as constant growth conditions are established, and so long as a period of quiescence could occur for a time sufficient to permit an oxygen gradient to develop within the growth medium. Therefore, although cell culture in flat surfaced plates, wells or dishes is preferred, adaptations of the present method to alternative growth surfaces, such as glass beads, could be readily adapted by one of ordinary skill in the art familiar with culturing cells using known techniques and procedures. Standard cell culture practices can be found, for example, in Freshney, RI in *Culture of Animal Cells: A Manual of Basic Technique*, ed. Liss, New York 1987, although each practitioner may have individual styles and practices.

By "culture," as it relates to "cell culture," is meant the in vitro, controlled growth of cells under constant and reproducible growth conditions in any suitable liquid culture medium which is known in the art of growing animal, plant or other cells that can be grown as attached cells or attached cell monolayers. The term "cultured" is used interchangeably with the terms "grown" or "in vitro." The term "cell culture" is intended to mean both the cells being cultured and the medium in which they are being cultured.

The "attached layer" preferably refers to a monolayer, meaning a layer of cells no more than a single cell in depth, preferably attached to the bottom surface of the plate or dish, although it may also be attached to a bead or other surface. The attached layer may, however, also refer to a layer of cells that have not formed a monolayer, e.g., cells that have formed clumps or piles of cells, so long as the oxygen gradient in the medium is adaptable to the present calculations.

The "medium" is preferably aqueous in nature comprising all essential nutrients, vitamins, minerals, sugars, salts, metabolites, essential amino acids, serum and the like for sustained survival, growth and division of the cells in culture, such as would be known in the art. Optimal temperature and pH of the medium would also be known, or could be rapidly determined, by such an individual. However, to be applicable to the present invention the medium must permit the diffusion of oxygen to the attached cell layer being sustained in the medium. Aqueous-based gel media could also be used in the present invention, so long as such material can support growth of the cells under constant and reproducible conditions, and so long as it permits diffusion of oxygen throughout the medium to the attached cell layer.

When the "medium" is treated in accordance with the methods of the present invention, it is intended that the medium is in quiescent contact with the cells in culture, not removed from them. The oxygen gradient could not be established if the medium were removed from the cells. Therefore, although the phosphorescence of the phosphor-containing medium is measured, it is essential to the method of the invention that the attached cell layer and the medium remain intact and that the medium remains quiescent. The calculations will be of greatest value if the medium has been in contact with the attached cells for a period of time sufficient to permit a measurable oxygen gradient to be established.

The medium either comprises a biocompatible phosphor (non-toxic to the cells) from the time the cells are initially inoculated, or a biocompatible phosphor is added to the cells, e.g., added to the medium directly or added to the medium when the medium is renewed after the cells have become established in culture. The application of the phosphor will be evident to one of ordinary skill, and can be determined based upon the type of cells and the medium in which they are grown. Prior to use, however, it is preferred that the toxicity of the selected phosphor be evaluated using viable sample cells, and that the solubility of the phosphor be ascertained in the culture medium.

"Phosphors" or "phosphorescent compounds" of the present invention include any $O_2$— sensitive compound which is soluble in the culture medium and non-toxic to the cells to be tested, and which upon excitation by a selected light source will produce a measurable phosphorescent light. The phosphorescent lifetime of the phosphors suitable for the present invention is diminished or reduced ("quenched") by $O_2$, specifically by the $O_2$ remaining in the oxygenated medium that has not been consumed by the cells. The preferred selected phosphors for use in cell culture are hydrophilic or water soluble, and more preferably biocompatible.

Although not intended to be limiting, suitable phosphorescent compounds include those described in U.S. Pat. No. 5,830,138 and co-pending U.S. Ser. No. 08/137,624, each of which is incorporated herein by reference, and as published in Vinogradov et al., *J. Chem. Soc., Perkin Trans.* 2:103–111 (1995). Preferred porphyrins of the present invention include those hydrophilic compounds having the following formula:

wherein $R_1$ is a hydrogen atom or a substituted or unsubstituted aryl; $R_2$ and $R_3$ are independently hydrogen or are linked together to form substituted or unsubstituted aryl; and M is a metal. In certain preferred embodiments, M is a metal selected from the group consisting of Zn, Al, Sn, Y, La, Lu, Pd, Pt and salts or derivatives thereof. Examples of such porphyrins, while not intended to be limiting, include, e.g., tetrabenzoporphyrin, tetranaphthoporphyrin, tetraanthraporphyrin, and derivatives thereof. More specifically, examples of applicable porphyrins, include, e.g., meso-tetraphenylated derivatives; tetraphenyltetrabenzoporphyrins; tetraphenyltetranaphthoporphyrins; meso-tetra-(4-carboxylphenyl) porphyrins; meso-tetraphenyltetrabenzoporphyrins; meso-10 tetraphenyltetranaphthoporphyrins; and tetrabenzoporphyrins.

More preferred for use in the present invention are known dendritic derivatives of the aforementioned porphyrin phosphors, which are highly efficient and highly soluble phosphorescent compounds surrounded by an inert globular structure. An example of such a compound is a derivatized metallotetrabenzoporphyrin compound, such as Pd-tetrabenzoporphyrin or Pd-meso-tetra-(4-carboxyphenyl)porphyrin. As disclosed in the '138 patent, substituent groups are known to impart desirable properties, such as solubility, to the preferred phosphorescent compounds.

The preferred porphyrin structures are surrounded by a three-dimensional supramolecular structure known as a dendrimer. It is known that one-, two-, and three-layer polyglutamate dendritic cages synthesized divergently around novel derivatized extended metalloporphyrin, oxygen-measuring, phosphor compounds provide phosphors which are highly water-soluble in a wide pH range and display a narrow distribution of phosphorescence lifetimes in deoxygenated water solutions.

The cells can be grown in any container suitable for attached cell growth and which can be maintained under conditions free of contaminants, e.g., dirt, dust, microbial, bacterial, viral, fungal or mycoplasma contaminants. Consequently, the cells can be grown on plates, flasks, roller bottles, and numerous other commercially-available containers designed specifically for cell growth. However, the methods of the present invention are particularly suited for measurements made on the effects of drugs on attached cells cultured in multi-well plates. Such plates can be any of the currently available varieties, but preferably are of high density plastic or other material with minimal permeability to oxygen, having covers, caps and/or lids to close and protect the wells from contaminants. Such covers, caps and/or lids may be oxygen permeable during the period of cell culture, so long as the constant oxygen environment is maintained at the air/medium interface.

Suitable plates would include single or multi-well plates having 2 to several thousand wells, preferably from 96 to 1536 wells, as shown in Burbaum et al, U.S. Pat. No. 5,908,776. Multi-well plates permit the rapid comparison of the drug test in one well with another, and are preferred in the present invention. The 96-well plates are particularly preferred. For the purposes of the present invention, the terms "plates," "dishes," "wells," "containers" or the like will be used interchangeably to mean that in which the cells are cultured.

The use of multi-well plates for the purpose of measuring oxygen consumption is novel, and the present method of measuring oxygen consumption will incorporate techniques for measuring phosphorescence lifetimes and relating them to oxygen pressure. If the multi-well plates are left without shaking or other disturbance of the medium above the cell layer (quiescence), oxygen consumption by the viable cells creates an oxygen gradient ranging from the air/medium interface at the surface of the medium to the layer immediately adjacent to the cells. It is a purpose of this invention to detect that gradient to permit the oxygen utilization to be calculated and compared against matching control cultures that have not been exposed to the drug or drug combination being tested.

The present method advantageously requires only very small sample sizes, since it relies upon an optical method that is not dependent on sample path length or light scattering. Measurements can be made in volumes as low as a few microliters in wells with diameters of less than 100 microns. The preferred depth of the well, at least in a 96-well plate, from the air/medium interface to the cell monolayer attached at the bottom of the well, is at least 1 mm, and is preferably about 2 mm to about 4 mm. However, the determination of the optimal amount of medium per well for a specific cell type will be known by one of ordinary skill familiar with culture a broad range of cell types under standard conditions. Such an individual will also know how often the media must be changed to preserve viability of the cells and accurate readings in the medium of the viable cells, and will be familiar with standard techniques for culturing cells without contamination (see, for example, Barnes et al. In *Cell Culture Methods for Molecular and Cell Biology*, ed. Liss, New York (1984); Eagle, *Science* 122:501–504 (1955); and Eagle, *Science* 130:432–437 (1959)).

II. The Drug or Test Compounds

The present invention is directed to the testing or evaluation of drugs. By "drug" is broadly meant any substance, compound or composition of matter, without limitation, which is introduced into the cell culture medium to determine its effect on the cells. Although preferably a medicament, the meaning of the term is limited only by that which is being tested by the present method. It may have an advantageous or disadvantageous effect on the cell, or no effect at all; this is the purpose of the test. The drug(s) being tested is introduced into each well at concentrations which are selected by the protocol of the drug evaluation. Different drugs can be introduced into different wells, and/or different concentrations can be introduced into different wells.

The drug being tested can be administered to the cells as a single dose, or as repeated dosages as is deemed appropriate by the individual of ordinary skill performing the evaluation.

The present methods and apparatus make it possible to measure the oxygen level at a specific point, or to establish determinative gradients by measuring the oxygen level throughout the cell culture media, i.e., at various layers or levels of the medium. As a result, measurements can be made in a matter of seconds or the oxygen gradient can be measured for selected cell samples over a period of minutes, hours, or even days, so long as the viable cells can be maintained under normal culture conditions and the oxygen gradient remains undisturbed in the medium. The time course of the measurements can be readily adapted by the evaluator to provide the breadth of information needed to determine the effect of the test drug on the cells, or to provide sufficient data to permit comparisons of the effect of the drug on a variety of cell types.

The methods and apparatus are also ideal for measuring the effect of one or more drugs in combination with another drug, or of one or more drugs in combination with one or more other substances, or of a drug administered with any other substance (carriers, adjuvants, enhancers, or the like).

III. M. Determination of the Oxygen Diffusion Gradient and Phosphorescence Lifetimes A. Quenching The phosphor-containing, cell culture medium is exposed to a modulated light source capable of exciting the phosphor to emit phosphorescent light, which permits measurement and calibration of both the phosphorescence intensity and delay time between the excitation light intensity and the phosphorescence emission (signal). Therefore, accurate determination of the frequency dependence of the signal amplitude and phase is used to calculate the oxygen pressure histogram for the culture medium using algorithms. The measured oxygen pressure histogram can then be used to accurately calculate the oxygen gradient, and therefore, the rate of oxygen consumption by the cells.

Phosphorescence quenching has been thoroughly verified as a method of measuring the oxygen dependence of cellular respiration (see, for example, Vanderkooi, J M, and Wilson D F, "A New Method for Measuring Oxygen Concentration of Biological Systems, in *Oxygen Transport to Tissue VIII*, Longmuir, ed., Plenum (August 1986); Vanderkooi, J M, et al., *J. Biol. Chem.* 262, No. 12:5476–5482 (April 1987); Wilson et al., *J. Biol. Chem.*, 263:2712–2718 (1988); Robiolio et al., *Am. J. Physiol.* 256 (6 Pt 1):C1207–1213 (June 1989); Wilson, D F, et al., *Adv. Exp. Med Biol.* 316:341–346 (1992); and Pawlowski, M, et al., *Adv. Exp. Med Biol.* 316:179–185 (1992). For detailed data on the calibration techniques and oxygen measurement capabilities of one widely used phosphor, see Lo et al., Analy. Biochem. 236:153–160 (1996). At constant temperature, phosphorescence lifetime is independent of the other parameters and composition of the sample.

It is important in the present invention to use a compound of known quenching constant and known lifetime at zero oxygen for a given temperature. Thus, once the compound and temperature are determined, calibration need only be made on a single occasion, after which the value can be used for all subsequent measurements involving that compound.

Measurements according to the present invention are rapid and highly reproducible. Less than 2 seconds are required for each measurement and current instruments have a measurement-to-measurement variability of less than 1 part in 1000. Due to the absolute calibration, equally low variability is attained among different samples having the same oxygen pressure.

B. Excitation

In accordance with the invention, a light source means, preferably a modulated light source, is employed for excitation of the soluble phosphor compound in the cell culture medium to a state of phosphorescence. A beam of excitation light is passed through the medium from any direction, i.e., top to bottom, bottom to top or through the sides, so long as the beam passes completely through the medium, equally exciting the phosphor at all layers of the medium. In a preferred embodiment, the light is passed through the medium from the top of the well. The emitted phosphorescence is then collected, either from above or below the well, so long as the phosphorescence is evenly distributed to the collection point.

Phosphorescence lifetime measurements use modulated excitation light, i.e., undulated sinusoidally, from 20 to 50,000 Hz, preferably from 50 to 35,000 Hz, most preferably from 100 to 20,000 Hz. The preferred measurements detect only those emissions that are at a longer wavelength and modulated at the same frequency.

The light source means can be provided by any of several different sources, including a flash lamp, a pulsed light emitting diode, or a pulsed laser. In the preferred mode, the light source is a light-emitting diode (LED), such as a laser diode. LEDs provide monochromatic light with a relatively broad bandwidth. The light is preferably passed through an interference filter to block the long wavelength "tail" in the emission of the LED, which might otherwise interfere with the measurements of the present invention. Solid state light sources can be readily modulated at the desired frequency and are monochromatic, i.e., light emission occurs primarily in either a broad band up to about 60 nm bandwidth at half height for LEDs or at a narrow band of 1 nm or less for laser diodes. As a result, minimal optical filtering is required for optimal application of such light to the measurement of phosphorescence lifetimes.

Modulation of the light can be achieved either by direct modulation of the light source or by passing the light through a modulation device, such as a flasher or a rotating wheel with slots through which the light may pass.

C. Measuring the Emitted Phosphorescence

The measurements of the present invention are readily adapted to very small sample sizes. The present optical method is not dependent on sample path length or light scattering. Measurements can easily be made in volumes as low as a few picoliters, and in spots with diameters of less than 20 microns.

Measurements of phosphorescence lifetime are independent of the concentration of the phosphor(s) in the medium, so long as the phosphor(s) is present in the medium at a concentration range needed for oxygen measurement. Within the functional concentration range, there is no significant "self quenching" due to energy transfer from triplet state to ground state phosphor molecules. This is because of the relatively large size and charge of the preferred dendrimer constructs. Measurements of phosphorescence lifetimes are also independent of absorption by other chromophores, such as hemoglobin, which may be present in the medium. Lifetime measurements are independent of changes in absorption and light scattering, as long as the changes do not occur during phosphorescence decay (<1 msec). This makes the method particularly effective in measuring oxygen in culture media, where it is often necessary to add fetal calf serum and/or other agents that may introduce colored components.

Based upon the principle that the beam of excitation light passed through the medium will equally excite the phosphors at all levels of the medium, and because the phosphorescence lifetime increases as the oxygen concentration in its immediate environment decreases, the calculated lifetimes will necessarily be proportionally longer for points in the medium nearest to the layer of viable cells. Phosphorescence may be measured by any available means in accordance with the present invention.

In general, two conventional methods for measuring phosphorescence lifetime (or decay time) are (i) the "pulse method" in the time domain, and (ii) the "phase method" in the frequency domain. In a time domain procedure, the phosphor-containing medium (the "sensor medium") is illuminated with a short flash of excitation light and the subsequent phosphorescence decay is measured by a time domain device or instrument. In a frequency domain procedure, excitation of the sensor medium is accomplished with a modulated light source, and the phase difference between excitation and emission is measured by a frequency domain device or instrument. Either measurement can be deconvoluted into the distribution of phosphorescence lifetimes in the medium and the fraction of the total phosphor with each lifetime. This lifetime and volume fraction distribution can then be converted into the fraction of the medium at each oxygen pressure (concentration), thereby determining the oxygen gradient, and from it the respiration rate of the cells following exposure to the drug being tested.

Phosphorescence lifetime from the measured decay and/or intensity is calculated, followed by calculation of oxygen partial pressure (concentration) or gradient in the culture medium from the oxygen relationship at each point in the medium to the phosphorescence lifetime and appropriate calibration constants, i.e., quenching constant, and lifetime in the absence of oxygen. Therefore, the collected phosphorescence decay data, for example, will be the summation of the phosphorescence decays for the phosphor(s) at all levels of the medium.

In the pulse method, a sample is excited by a short pulse of light and the resulting phosphorescence emission in the longer wavelength is an exponentially decaying function with a measurable rate of decline. The pulse method is used in most of the existing instruments for oxygen measurement.

In the phase method, a sample is excited with modulated light, with absorbed light being re-emitted as phosphorescence after a certain delay period. As a result, phosphorescent emission is also modulated with the same frequency, but delayed in time (phase shifted) with respect to the excitation wave. The resulting phase shift, found experimentally, is used to calculate the phosphorescence lifetime.

The phase method is preferably used in an embodiment of the present invention because frequency lock amplification can be advantageously used to greatly increase sensitivity. Interference from ambient light is greatly decreased by this method, since only signals with the same modulation frequency as the excitation light are amplified, which largely eliminates interference by other ambient light sources.

The measurement of phosphorescence lifetimes can be fully automated, for example by using light guides to read individual wells or a video camera to read some or all of the wells at one time. By using phosphorescence quenching, it is possible to determine the phosphorescence lifetime distribution profile for the cell culture by deconvolution of the data. This data can then be used to calculate the oxygen gradient formed by the oxygen diffusion within the still medium. The oxygen diffusion gradient is a direct measure of the oxygen consumption rate for the attached cell layer. The method allows very rapid measurements of the respiratory rate of the cells under the selected conditions, without necessarily using multiple readings to establish a time course of oxygen use in the medium.

Suitable automated microplate readers are those capable of measuring phosphorescence in several channels simultaneously. As previously noted, the measurements may be made either through the top or bottom of the well, which ever is more suited to the particular apparatus used to make the measurement, so long as the phosphorescence is evenly and reproducably collected. The reader simultaneously reads the multiple channels, then either (i) the detector bar is moved into position to permit the reading of the next row of wells, or (ii) the plate is moved until the next row of wells is in position for the reader to make the next reading or set of readings. In one embodiment of the present invention, as exemplified by a 96-well plate, each set of eight readings would require about 1 second to complete, allowing all 96 wells of a plate to be read in 12 to 16 seconds.

The values of the phosphorescence intensities and lifetimes are tabulated for later analysis, and the measurements are repeated as often as necessary until the desired endpoint is reached. The time at which the data is measured is recorded, from which the rate of oxygen removal from the medium (respiratory rate) can be calculated. Measurements of the phosphorescence lifetimes are extremely reproducible from instrument to instrument, due partly to the absolute calibration and partly to the nature of lifetime measurements.

In practice, the phosphorescence is collected, passed through appropriate filters and carried to the detector. The phosphorometer photodetector (PD) or device for collecting and measuring the emitted phosphorescent light, can be, for example, a silicon photodiode with a built-in preamp, an avalanche photodiode, a photomultiplier, or other known PD devices such as would be known to the practitioner. The photodetector output is amplified to provide a signal of optimal voltage for digitizing by the analog-to-digital converter (ADC). A photodiode with an internal amplifier is selected for the optimal light sensitive surface area and lowest noise level.

For example, the Hamamatsu Corporation HC1120 analog photomultiplier tube assembly with an R3823 photomultiplier has an appropriate surface area (more than 5 mm$^2$) and excellent photosensitivity, in the 500 v to 900 nm wavelength range. Thus, it embodies a preferred photodetector for use in the present invention.

The signal from the photodetector can be further amplified with an AC-coupled operational amplifier. The quality of the phase detection depends on the reduction of noise level in the photodiode output signal. After amplification, the output signal is delivered to the analog multiplexer and then input into the ADC for digitizing.

In yet another embodiment of the present invention, the emitted light is filtered and detected with an avalanche photodiode. The output of the detector is amplified and passed to a 16 bit (or greater) Delta-Sigma digitizer operating at 48 or 96 kHz. Data collection from the digitizer is synchronized with readings of the tabulated values into the D/A unit providing the driving current for the light source. Data collection is always begun at the same point in the table of values controlling the LED light output.

The digitized phosphorescence data is transferred to a specific file in memory, preferably a 1024×32 bit block of memory. Further data sets (a total of m data sets) are added to the same memory area, always beginning at the same point. Because the collected data are "locked" to the table of values being used to control the excitation light, only signals of exactly the same frequencies as those used to generate the excitation signal are summed positively. All other signals (and noise) are summed destructively, and their amplitudes decrease as the number of scans (m) increases. Noise amplitude, on the other hand, increases only as the square root of the number of scans summed ($m^{1/2}$), thus providing increase in signal-to-noise ratio.

In a preferred, exemplified configuration, 20 data sets would be summed. Assuming that each data set is approximately 20 msec long (1024 points at 48 kHz), summing the 20 sets would require less than 0.5 seconds.

In a preferred embodiment, the phosphorometer or device for measuring the emitted phosporescence, contains a core digital signal processor (DSP) with sufficient memory (RAM and ROM) to carry out the indicated calculations and to control both the output of the excitation light source and collection of the phosphorescence data. In addition, the device contains Delta-Sigma signal processors (DSP)(both A/D and D/A) for converting calculated data tables to current for the excitation light (D/A), and for digitizing the photodetector output (A/D) for digital analysis. The DSP, A/D and D/A are preferably 16 bit or greater, and the memory is preferably able to operate in 32 bit words or greater.

A preferred instrument for practice of the present invention can be constructed from Analog Devices ADSP-2181 and AL 1847 Stereo Codex with stereo high precision 48 kHz, 16 bit, 20 Delta-Sigma ADCs with 64× oversampling.

A sine wave signal of the desired frequency can be generated by the DSP using a 16 bit DAC and smoothing circuits of the Stereo Codex. The resulting signal will control the current in the LED or laser diode driving circuit. The LED driver circuit is designed to provide a greater than 90% modulation of light output. This is accomplished by adding a DC signal to the sinusoidal signal, such that the minimum current is just above the threshold for light emission. Above this threshold, the light output is a nearly linear function of the current through the LED.

The LED is modulated to provide light that is a sum of many sinusoidal waves of equal amplitude as follows:

$$Ex(t) = B + \sum_{k}^{N} A \cdot \sin(2\pi f_k t) \qquad \text{(Eq. 1)}$$

The frequencies are selected such that the cycle times for the lower frequencies are multiples of the highest frequency. For example, if a set were selected which contains 200 frequencies, spaced between 100 and 20,000 Hz, then: $f_k = f_1 \cdot k$, when the $f_1 = 100$ Hz, $k = 1 \ldots N$, and $N = 200$.

The resulting waveform (Eq. 1) presents "nodes" or points at which all of the component waveforms pass through zero. The time between nodes is set by the lowest frequency used. These frequencies are digitally summed, and a DC offset (B, Eq. 1) is added to provide a table of values in which all values are positive. The current for driving the LEDs is obtained, for example, by sequentially reading the values in the data table into a Digital to Analog converter (preferably, 16 bits and 48 kHz) and by amplifying the signal to provide the driving current for the light source (LEDs).

IV. Calculating the Phosphorescent Lifetime and Oxygen Distribution

When an attached layer of viable cells is covered with medium having a depth "L," under constant temperature and steady state respiration, the oxygen concentration within the medium linearly decreases from the air/medium interface ($O_2$max) to the layer immediately adjacent to the cell layer ($O_2$min). Thus, a constant gradient is formed, which is informative of the cells respiratory rate. Consequently, the oxygen concentration gradient, in combination with the diffusion constant for oxygen, can be used to accurately calculate the rate of oxygen consumption per unit area of cell culture. This absolute calibration, combined with the lack of interference due to the negligible alterations in sample position, absorption, fluorescence, and light scattering, makes the present inventive method ideal for automated measurements.

To calculate and understand the phosphorescence lifetime distribution, and thus the oxygen distribution within the sample, the first step is to extract the dependence of the phosphorescence amplitude (a) and the phase angle ($\phi$ on the modulation frequency.

Since all modulation frequencies are mixed in the excitation light, the emitted signal contains a spectrum of all the resulting phosphorescent lifetimes within the medium at a given point in time. Thus, following delivery of the excitation light (Eq. 1), the phosphorescence response is calculated as follows:

$$Em(t) = b + \sum_{k}^{N} a_k \sin(2\pi f_k t - \phi_k) \quad \text{(Eq. 2)}$$

where $a_k$ represents the phosphorescence amplitude and $\phi_k$ represents the phase angle for each individual frequency used in the excitation array. Therefore, by rewriting Eq. 2, using trivial trigonometry, the emitted signal is calculated as follows:

$$Em(t) = b + \sum_{k}^{N} [a_k \sin(2\pi f_k t)\cos(\phi_k) - a_k \sin(\phi_k)\cos(2\pi f_k t)] \quad \text{(Eq. 3)}$$

or $$Em(t) = \sum_{k}^{N} [P0(f_k)\sin(2\pi f_k t) - P1(f_k)\cos(2\pi f_k t)] + P2$$

where $P0(f_k)=a_k \cos(\phi_k)$, $P1(f_k)=a_k \sin(\phi_k)$ and $P2=b$.

In the present invention, P0(f) and P1(C) represent functions of the excitation frequency f (or frequencies $f_k$ if a frequency set was used). Using $\chi^2$-fitting ("least squares") of the phosphorescence signal, with the probe function in the form of Eq. 3, the dependencies of P0 and P1 on the modulation frequency are recovered. Alternatively, Fourier techniques can be used to obtain the dependencies. However, the disclosed calculations based upon linear algebra are, in this case, by far, more accurate, robust and fast because P0, P1 and P2 participate in the probe function (Eq.3) as simple linear parameters.

Once the vectors (or arrays) $P0(f_k)$ and $P1(f_k)$ are obtained, they are analyzed to determine the phosphorescence lifetime distribution for the selected sample. The distribution or lifetime spectrum is directly converted into the distribution of oxygen concentrations using Stern Volmer equation.

The phosphorescence emitted at a selected time or over a time course from a sample, comprising a heterogeneous array of lifetimes, following excitation of the sample with a flash of light, is described as an integral in accordance with Eq. 4, known as the Laplace transform.

$$I(t) = \int_0^\infty g(\tau)\exp\left(-\frac{t}{\tau}\right)d\tau \quad \text{(Eq. 4)}$$

Function g($\tau$) describes lifetime distribution or spectrum, while exp(t/$\tau$) presents what is commonly referred to as a "transform kernel." A "transform kernel" is a set of functions over which the linear integral transform is defined.

The kernel of the Laplace transform is the set of real exponentials. This kernel is incomplete, and so there are examples of the objects (lifetime distributions) which cannot be recovered from the Laplace images. Various numerical methods are used to invert "incomplete" integral transforms. The most probable solution for Laplace transform inversion can be obtained using the Maximum Entropy Method.

In a frequency domain the dependencies of the parameters P0 and P1 on the modulation frequency are provided by the similar integrals (Eq. 5), which are the Fourier images (sine and cosine transforms respectively) of the Laplace integral (Eq. 4):

$$P0(f) = \int_0^\infty g(\tau) \cdot \theta(f, \tau) d\tau \quad \theta(f, \tau) = \frac{\tau}{1+\omega^2\tau^2} \quad \text{(Eq. 5)}$$

$$P1(f) = \int_0^\infty g(\tau) \cdot \psi(f, \tau) d\tau \quad \psi(f, \tau) = \frac{\omega\tau^2}{1+\omega^2\tau^2}$$

$$\omega = 2\pi f$$

Since the only difference between the integrals Eq. 4 and Eq. 5 are the transform kernels, while the lifetime spectrum remains unchanged, the existing algorithms for the Laplace transform inversion can be applied to the recovery of g($\tau$) from the data presented by P0(f) and P1(f) (Eq. 5). In such algorithms, the shape of continuous g($\tau$) is approximated by a finite dimension histogram. The histogram represents an array of numbers, p={$p_n$}, corresponding to the fixed lifetimes {$\tau_n$} (a "lifetime grid"), spanned in the range zero to ($\tau_{max}$). Maximal lifetime ($\tau_{max}$) corresponds to the phosphorescence lifetime in the absolute absence of oxygen, and thus it is the longest possible lifetime presented in the signal. The goal of the numerical methods is finding of the histogram p which maximally resembles the shape of g($\tau$).

Quenching of phosphorescence by oxygen is determined by the frequency of collision between the excited triplet state molecules and oxygen. This means the measured phosphorescence lifetime may be converted to oxygen pressure according to the Stem-Volmer relationship, which is stated as follows:

$$\tau_o/\tau = 1 + k_q \cdot \tau_o \cdot PO_2 \quad \text{(Eq. 6)}$$

where $\tau_o$ and $\tau$ are the phosphorescence lifetimes in the absence of oxygen, $PO_2$ is the oxygen pressure for a lifetime of $\tau$, and $k_q$ is the quenching constant. The constant $k_q$ is related to the frequency of collisions between the excited triplet state molecules and molecular oxygen and the probability of energy transfer occurring when these molecules collide. Use of the Stem-Volmer relationship is also set forth in U.S. Pat. No. 5,501,225, which is herein incorporated by reference.

The present invention is further described in the following examples. These examples are not to be construed as limiting the scope of the appended claims.

EXAMPLES

Example 1

An Exemplar Calculation of Cell Respiration

The following formulae describe the relationships of the respiratory rate of cells growing as an attached culture to a flat surface and the oxygen concentration at different depths in the culture medium over the layer of cells:

$$\Delta O_2 = r \cdot p \cdot d/D \quad \text{(Eq. 7)}$$

By example, the following parameters, when substituted into Eq. 7, demonstrate the method of the present invention. When d=the thickness of the layer of medium (diffusion distance), and D is the oxygen diffusion constant at 38° C. ($2\times10^{-5}$ cm$^2$/sec), and when the oxygen consumption per cell per second is r=$5\times10^{-17}$ moles $O_2$/cell/sec; and when the cells per square centimeter (cm$^2$) at confluence are p=$4\times10^5$ cells/cm$^2$; then the oxygen consumption per second (r·p)= $20\times10^{-12}$ moles $O_2$/cm$^2$/sec.

By substituting into the diffusion equation (Eq. 7) a value of $\Delta O_2$, equal to that at air saturation, the distance (thickness of the layer of medium) at which the diffusion gradient is equal to the oxygen ($O_2$) available in the air can be calculated. At air saturation and 38° C., the oxygen content is $180 \times 10^{-6}$ M or $180 \times 10^{-9}$ moles/cm. Thus: $(180 \times 10^{-9}$ moles/cm)·$(2 \times 10-5$ cm$^2$/sec)/$(20 \times 10^{-12}$ moles/cm$^2$/sec)=d= 1.8 mm. Thus, for the chosen cell density the oxygen pressure in the medium adjacent to the cells is near zero when the cells are covered with an undisturbed layer of medium about 1.8 mm deep. Optimal thickness of the layer of medium for avoiding cellular hypoxia can be readily chosen by anyone skilled in the art using our apparatus because our apparatus directly measures both the oxygen gradient and of the oxygen concentration at the layer of growing cells.

Measurements of the oxygen pressure in the medium display a nearly linear gradient from the surface of the medium to the layer of cells. The gradient formed is a direct measure of the respiratory rate of the cells, and can be used to measure cell growth, viability, death, morbidity, metabolic alteration, etc. Because this is a continuously regenerated steady state, it is always present and can be measured at any time without disturbing the cell culture. Thus, in accordance with the present invention, it is possible to non-destructively follow respiration in a cell culture for many days.

For example, the rate of oxygen consumption by a layer of cells can be calculated from the measured oxygen concentration gradient. When the cells are covered by a layer of medium 1.5 mm thick (d=0.15 cm) and the measured value of $\Delta O_2$ is $100 \times 10^{-9}$ moles/cm, substitution into Eq. 7 would result in the following calculation:

$(100 \times 10^{-9}$ moles/cm$)=(Y$ moles $O_2$/cm$^2$/sec$)\cdot(0.15$ cm$)/(2 \times 10^{-5}$ cm$^2$/sec$)$, from which the rate of oxygen consumption (Y)=$13.3 \times 10^{-12}$ moles/cm$^2$/sec.

Example 2

The Mathematical Relationship between Phase Shift and Phosphorescence Lifetime

In the phase approach, the mathematical relationship between phase shift and phosphorescence lifetime can be described as follows:

$$\tan \phi = 2\pi f \cdot t \quad \text{(Eq. 8)}$$

where $\phi$=phase difference (phase shift) between excitation and emission sine waves at the modulation frequency, f, and t=lifetime of phosphorescent decay.

It can be shown that for a given signal-to-noise ratio, the lowest error in the estimation of the phosphorescence lifetime is obtained when the phase shift is about 26°.

It follows from the Stem-Volmer relationship and the diffusion equation that to maintain the phase shift of about 26° for all oxygen concentrations in the range, it is necessary to be able to vary the modulation frequencies from 20 Hz to 20,000 Hz. However, it is preferred that modulation frequencies be controlled from 100 Hz to 20,000 Hz, and instrumentation be employed which can measure phosphorescence lifetime of a given fixed frequency and/or at a first estimate optimal frequency for a given value of the phase shift (26°), and to then proceed with actual lifetime measurements. To ensure oxygen measurements are accurate to air saturation and above (lifetimes as short as <15 $\mu$sec), the phosphorescence signal is preferably sampled (digitized) at 48 kHz or greater.

The digital signals will be processed to extract the signal strength (magnitude) and phase relative to the excitation light. Calculations of the phosphorescent lifetime and oxygen pressure will follow the above-described procedures.

According to our preferred algorithm, a first approximation $p_0$ is done by applying a fast quadratic programming algorithm, based on 0-order Tikhonov's regularization. The solution is attained by maximizing a quadratic functional H(p), constructed in the following form:

$$H(p) = -\chi^2(p) - \mu(p,p) \quad \text{(Eq. 9)}$$

where $\chi^2(p) = -(\text{grad}_0, p) + \frac{1}{2}(p, Qp)$ is a standard least squares function and $\mu(p, p)$ is a Tikhonov's 0-order smoothness regularizer. Parentheses in the expression $\mu(p, p)$, and in similar instances, denote the scalar product of the enclosed vectors, which are shown in bold. The vector $\text{grad}_0$ is an anti-gradient of $\chi^2(p)$ calculated at the origin, and Q is a Hessian matrix (matrix of the second partial derivatives of $\chi^2(p)$). For a small value of $\mu$ in the regularizer, chosen depending on the value of noise in the data, the optimization of H(p) can be effectively performed using a robust quadratic algorithm proposed by R. Shrager, *Numerical Mathematics* 15:41 (1972). This algorithm converges in the finite amount of steps and assures non-negativity of the solution $p_0$.

After the initial solution is found, the following improvement in the shape of p is achieved recursively by minimizing another functional:

$$G(p) = \chi^2(p) - \mu E(p) \quad \text{(Eq. 10)}$$

using the same algorithm and solution vector $p_i$ obtained at the previous step.

In subsequent Eq. 11, functional $E(p) = -(p, \log(p))$ refers to the Shannon-Janes entropy. The minimization of G(p) is equal to the maximization of S(p):

$$S(p) = -G(p)/\mu = E(p) - \chi^2(p)/\mu \quad \text{(Eq. 11)}$$

and, after replacing $1/\mu = \lambda$, since $\mu$ is a simple constant, Eq. 11 transforms into:

$$S(p) = E(p) - \lambda \cdot \chi^2(p) \quad \text{(Eq. 12)}$$

The value of the regularization constant is dependent on the signal to noise in the data, but is constant for computational analysis of any one data set.

The maximization of the functional S(p) is known as Maximum Entropy Method (MEM), which according to the information theory allows the recovery of the "best" uncorrelated histogram p from the noisy data.

Figure 1:
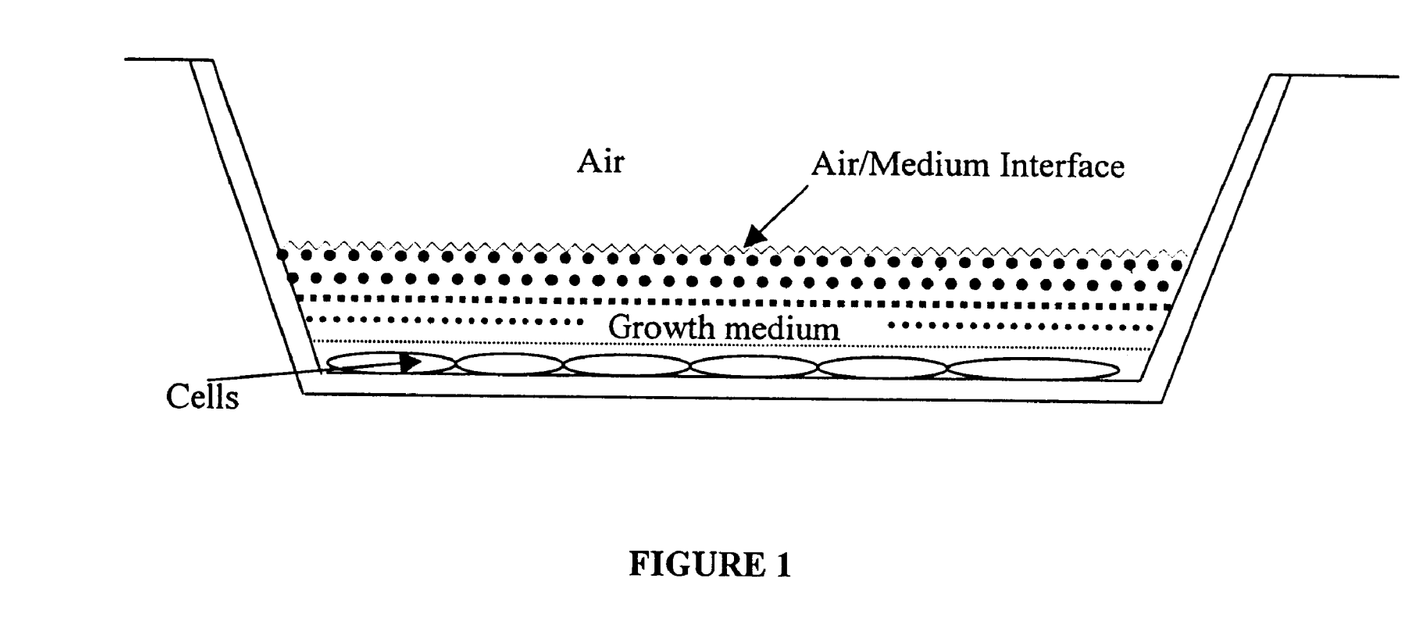
FIG. 1 is a cross-sectional view of a single well containing attached cells in a culture medium. Dots represent the oxygen concentration throughout the medium, while the relative thickness of the dots represents the oxygen gradient within the medium.
Figure 2:
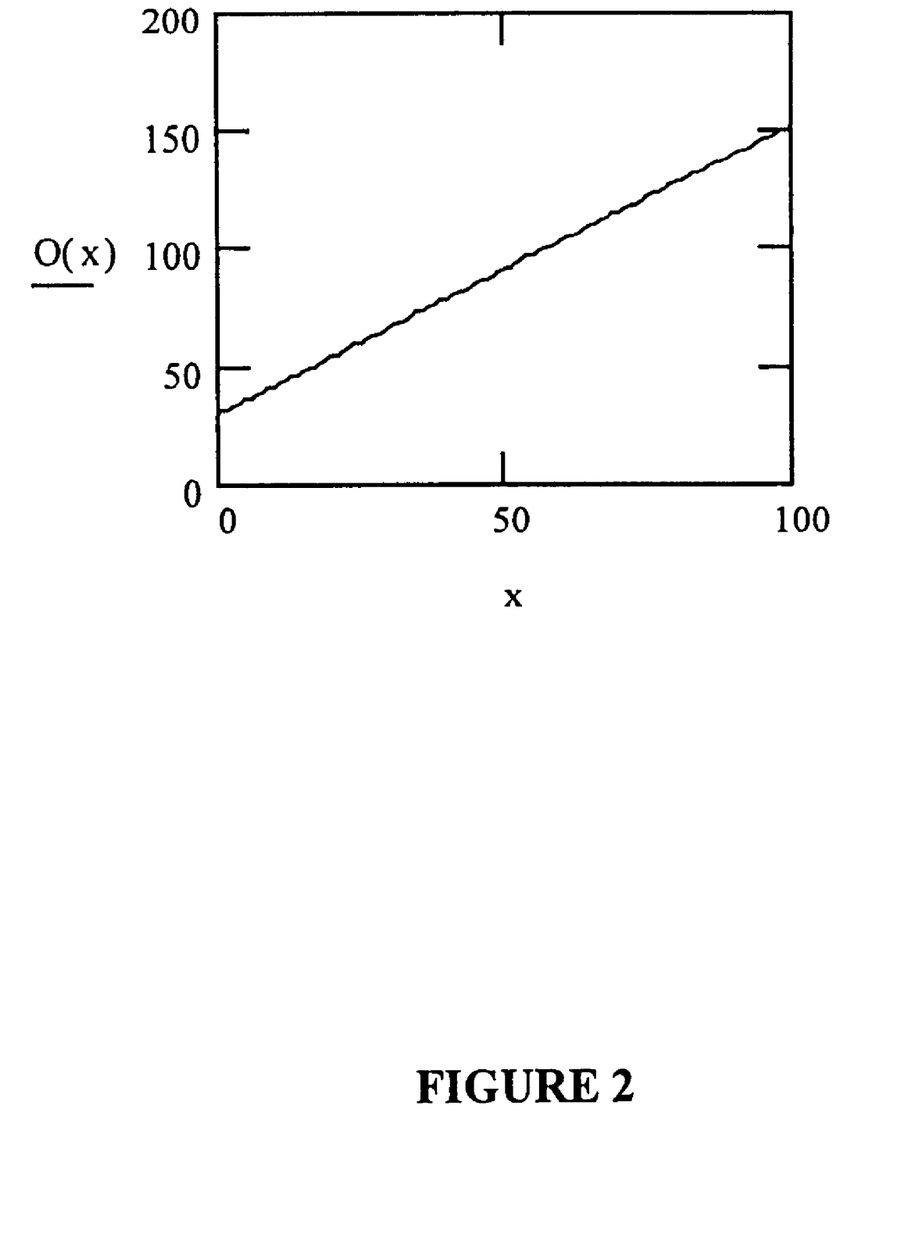
FIG. 2 is a graphical representation of oxygen concentration in the cell culture medium versus the distance of a point in the medium from the cell layer.
Figure 3:
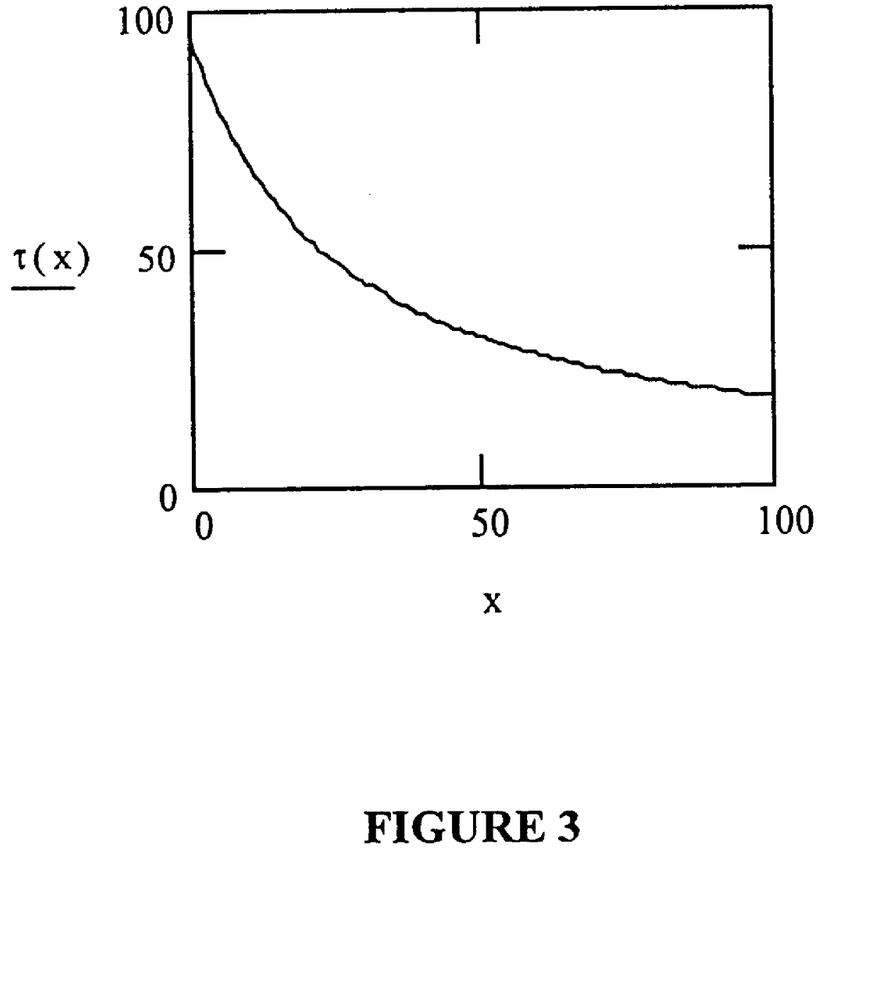
FIG. 3 is a graphical representation of phosphorescence lifetime of the phosphor versus distance of a point in the medium from the cell layer.

For $O_2^{max} = 152$ Torr (which is equal to the oxygen pressure in the atmosphere at sea level (20% of 760 Torr)), when $O_2^{min} = 30$ Torr, and x is the distance from the cell surface (expressed in % of the total distance L), the oxygen concentration O(x) will increase as shown in FIG. 2.

Figure 4:
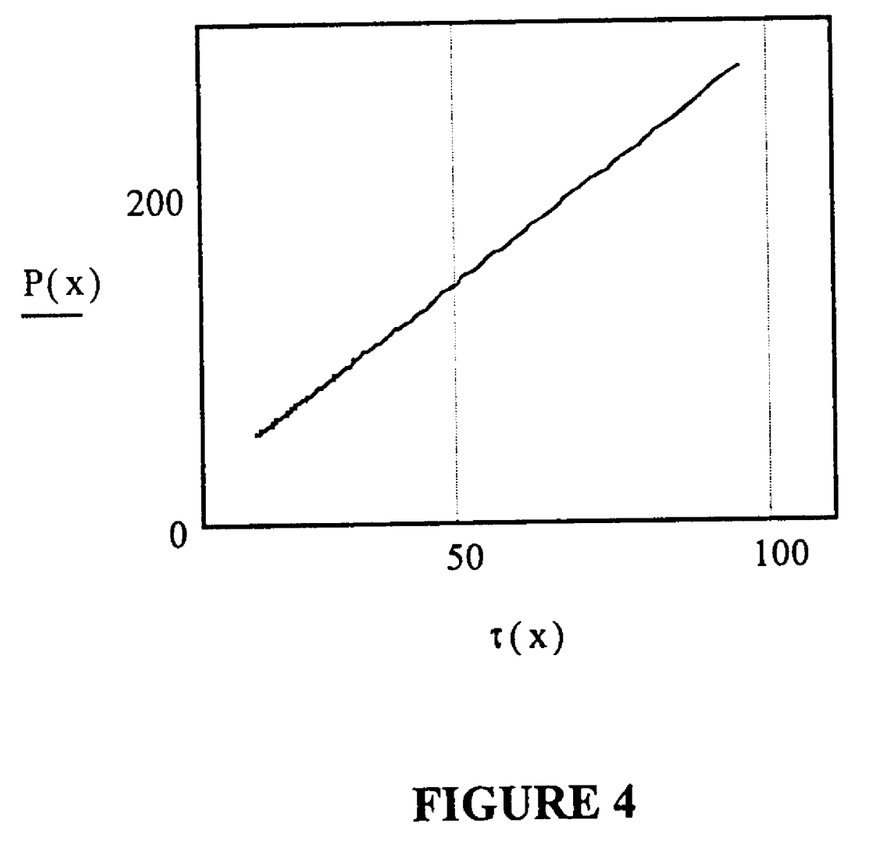
FIG. 4 is a graphical representation of intensity of phosphorescence (P(x)) versus lifetime.

The phosphorescence lifetime, being the reciprocal of oxygen concentration, will hyperbolically decrease with increase of the distance x as shown in FIG. 4, which is a graph of phosphorescence lifetime versus distance from the cell layer. Lifetime is given in microseconds, assuming $\tau_0 = 350$ $\mu$sec and $K_a = 350$ Torr$^{-1}$ sec$^{-1}$, as the characteristics for the phosphor.

However, the relative intensity $P(\tau)$ of the phosphorescence lifetime (e.g., lifetime spectrum) is proportional to the lifetime itself, and thus $P(\tau)$—the lifetime spectrum—will have a simple linear profile (FIG. 4), with the slope directly related to the oxygen gradient in the studied sample. Knowing that the distribution must have linear shape will greatly improve the accuracy and speed of the MEM recovery, as any a prior information. The information about the distribution shape can be directly incorporated into the recovery algorithm, thus permitting rapid and efficient calculation of the oxygen gradients in the studied samples and providing a reliable, quantifiable and objective determination of the effect of a drug or drugs on the cells.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method for determining an effect of at least one drug on respiration rate of cells in an attached culture of cells comprising:
    a. dissolving a phosphorescent compound in a culture medium comprising an attached culture of cells at the bottom of a vessel containing same, wherein a quenching constant and lifetime at zero oxygen are known or previously determined for the phosphorescent compound at temperature (t);
    b. introducing the at least one drug, for which an effect on the cells is being determined, into the culture medium;
    c. illuminating the cell culture and culture medium with a pulsed or modulated excitation light at an intensity and frequency sufficient to cause the phosphorescent compound to emit a measurable phosphorescence;
    d. measuring the emitted phosphorescence at a point in the culture medium between the attached cell layer and air/medium interface;
    e. calculating the phosphorescence lifetime and oxygen concentration gradient in the medium; and
    comparing the calculated phosphorescence lifetime and oxygen concentration gradient with that of a comparable cell culture without the at least one drug, thereby determining the effect of the at least one drug on the respiration rate of the cells at temperature (t).

2. The method of claim 1, wherein the attached cells are animal cells.

3. The method of claim 1, wherein the cells are attached to a flat bottomed plate or well.

4. The method of claim 3, wherein the change of mean partial pressure is used to determine morbidity of the cells, growth of the cells, or metabolic alteration of the cells, in response to the drug.

5. The method of claim 1, comprising determining (i) the mean partial pressure of oxygen in the culture medium, and (ii) any change in partial pressure, and thereby determining (iii) any change in the respiration rate of the cells.

6. The method of claim 1, comprising determining the distribution curve of oxygen concentrations throughout the culture medium, thereby permitting determination of respiration rate of the cells.

7. The method of claim 1, wherein the excitation light is provided by a light source selected from the group consisting of flash lamp, pulsed light emitting diode, and pulsed laser to illuminate the culture medium at a selected frequency.

8. The method of claim 1, wherein the emitted phosphorescence is measured by a time domain device or by a frequency domain device.

9. The method of claim 1, further comprising repeating the steps of (c) through (f).

10. The method of claim 1, further comprising converting the measured phosphorescence into digital values.

11. The method of claim 1, comprising measuring the emitted phosphorescence by a device selected from the group consisting of a photomultiplier, an avalanche photodiode, and a photodiode.

12. The method of claim 1, further comprising calculating rate of oxygen consumption of the cells by a process which comprises reconstructing an oxygen concentration gradient by deconvoluting distribution of lifetimes data into underlying distribution of exponentials.

13. The method of claim 12, wherein reconstruction of the oxygen concentration gradient permits determination of the rate of oxygen consumption of the cells.

14. The method of claim 1, wherein the phosphorescent compound does not chemically react with the cells or culture medium, and does not affect the growth, viability or morbidity of the cells.

15. The method of claim 1, further comprising a high sensitivity video camera for measuring the emitted phosphorescence from the phosphorescent compound.

16. The method of claim 1, wherein one or more steps of the method are automated.

17. The method of claim 1, wherein the drug is a combination of more than one composition.

18. The method of claim 1, wherein the phosphorescent compound is a porphyrin compound having the formula:

wherein $R_1$ is a hydrogen atom or a substituted or unsubstituted aryl; $R_2$ and $R_3$ are independently hydrogen or are linked together to form substituted or unsubstituted aryl; and M is a metal.

19. The method of claim 18, wherein M is a metal selected from the group consisting of Zn, Al, Sn, Y, La, Lu, Pd, and Pt which is prepared from the metal salts or derivatives thereof.

20. The method of claim 19 wherein the porphyrin is selected from the group consisting of tetrabenzoporphyrin, tetranaphthoporphyrin, tetraanthraporphyrin, and derivatives thereof.

21. The method of claim 20, wherein in the porphyrin is selected from the group consisting of a meso-tetraphenylated derivative; tetraphenyltetra benzoporphyrin; tetraphenyltetranaphthoporphyrin; meso-tetra-(4-carboxylphenyl)porphyrin; meso-tetraphenyltetrabenzoporphyrin; meso-tetraphenyltetranaphthoporphyrin; and tetrabenzoporphyrin.

22. The method of claim 20 wherein the porphyrin is a first, second, third, fourth or fifth generation dendrimer.

23. The method of claim 22, wherein the dendrimer comprises polyglutamate dendritic cages.

24. The method of claim 1, wherein the effect on the cells is determined for a single drug.

25. The method of claim 1, wherein the effect on the cells is determined for a combination comprising more than one drug.

26. The method of claim 1, wherein emitted phosphorescence is measured at a single point in the cell culture medium.

27. The method of claim 1, wherein emitted phosphorescence is measured as an oxygen gradient by simultaneously determining the oxygen concentration at points throughout the cell culture medium.

* * * * *